US010772592B2

(12) United States Patent
Sano et al.

(10) Patent No.: US 10,772,592 B2
(45) Date of Patent: Sep. 15, 2020

(54) X-RAY PHASE CONTRAST IMAGING APPARATUS

(71) Applicants: Shimadzu Corporation, Kyoto (JP); OSAKA UNIVERSITY, Suita-shi (JP)

(72) Inventors: Satoshi Sano, Kyoto (JP); Koichi Tanabe, Kyoto (JP); Toshinori Yoshimuta, Kyoto (JP); Kenji Kimura, Kyoto (JP); Hiroyuki Kishihara, Kyoto (JP); Yukihisa Wada, Kyoto (JP); Takuro Izumi, Kyoto (JP); Taro Shirai, Kyoto (JP); Takahiro Doki, Kyoto (JP); Akira Horiba, Kyoto (JP); Takayoshi Shimura, Osaka (JP); Heiji Watanabe, Osaka (JP); Takuji Hosoi, Suita (JP)

(73) Assignees: Shimadzu Corporation, Nishinokyo-Kuwabaracho, Nakagyo-ku, Kyoto-shi, Kyoto (JP); OSAKA UNIVERSITY, Yamadaoka, Suita-shi, Osaka (JP)

( * ) Notice: Subject to any disclaimer, the term of this patent is extended or adjusted under 35 U.S.C. 154(b) by 0 days.

(21) Appl. No.: 16/321,297

(22) PCT Filed: Jul. 10, 2017

(86) PCT No.: PCT/JP2017/025143
§ 371 (c)(1),
(2) Date: Jan. 28, 2019

(87) PCT Pub. No.: WO2018/020999
PCT Pub. Date: Feb. 1, 2018

(65) Prior Publication Data
US 2019/0167219 A1    Jun. 6, 2019

(30) Foreign Application Priority Data
Jul. 28, 2016 (JP) .................................. 2016-148428

(51) Int. Cl.
*A61B 6/00* (2006.01)
*G01N 23/041* (2018.01)

(52) U.S. Cl.
CPC ............ *A61B 6/484* (2013.01); *A61B 6/4035* (2013.01); *A61B 6/4291* (2013.01); *G01N 23/041* (2018.02)

(58) Field of Classification Search
CPC ..... A61B 6/4035; A61B 6/4291; A61B 6/484; A61B 6/5258; G01N 23/041
See application file for complete search history.

(56) References Cited

U.S. PATENT DOCUMENTS

2013/0083893 A1* 4/2013 Ishii ..................... A61B 6/4291
378/62
2013/0094625 A1* 4/2013 Huang ................... A61B 6/484
378/6
(Continued)

FOREIGN PATENT DOCUMENTS

JP    2012-016370 A    1/2012

OTHER PUBLICATIONS

Atsushi Momose, Wataru Yashiro, Hiroaki Kuwabara, and Katsuyuki Kawabata, "Grating-Based X-ray Phase Imaging Using Multiline X-ray Source", Japanese Journal of Applied Physics 48 (2009) 076512, pp. 076512-1 to 076512-5.

(Continued)

*Primary Examiner* — Chih-Cheng Kao
(74) *Attorney, Agent, or Firm* — Muir Patent Law, PLLC

(57) ABSTRACT

This X-ray phase contrast imaging apparatus (100) includes an X-ray source (1) that radiates continuous X-rays, a first grating (3) that forms a self-image, a second grating (4), a detector (5) that detects the continuous X-rays, and a third grating (2) arranged between the detector (5) and the first grating 3. The first grating (3), the second grating (4), and (Continued)

the third grating (2) are arranged so as to satisfy conditions of predetermined formulas.

6 Claims, 5 Drawing Sheets

(56) References Cited

U.S. PATENT DOCUMENTS

2016/0356730 A1* 12/2016 Handa .................... A61B 6/484
2018/0180558 A1*  6/2018 Sano ..................... G01N 23/041

OTHER PUBLICATIONS

Written Opinion by the International Search Authority dated Oct. 3, 2017 for PCT application No. PCT/JP2017/025143, (submitted with a machine translation).
International Search Report dated Oct. 3, 2017 for PCT application No. PCT/JP2017/025143.

* cited by examiner (FIRST EMBODIMENT)

RELATIONSHIP BETWEEN FIRST GRATING AND SECOND GRATING

RELATIONSHIP BETWEEN THIRD GRATING AND SECOND GRATING

SIGNAL INTENSITY CHANGES UNDER FRINGE SCANNING METHOD

SIGNAL INTENSITY CHANGES UNDER METHOD USING FOURIER TRANSFORM METHOD (SECOND EMBODIMENT)

X-RAY PHASE CONTRAST IMAGING APPARATUS

TECHNICAL FIELD

The present invention relates to an X-ray phase contrast imaging apparatus.

BACKGROUND ART

Conventionally, an X-ray phase contrast imaging apparatus is known. Such an X-ray phase contrast imaging apparatus is disclosed in Japanese Patent Laid-Open No. 2012-16370, for example.

Japanese Patent Laid-Open No. 2012-16370 discloses an X-ray imaging apparatus (X-ray phase contrast imaging apparatus) that images the inside of a subject using the phase contrast of X-rays that have passed through the subject. This X-ray imaging apparatus can image a light element object and a soft tissue of a living body that are unlikely to absorb X-rays by imaging the inside of the subject using the phase contrast of the X-rays instead of the amount of absorption of the X-rays.

This X-ray imaging apparatus includes an X-ray source, gratings, and an X-ray image detector. The X-ray source, the gratings, and the X-ray image detector are arranged side by side in this order in the irradiation axis direction of the X-ray source.

In this X-ray imaging apparatus, the arrangement of the X-ray source, the gratings, and the X-ray image detector is determined by mathematical formulas. In the mathematical formulas, it is necessary to substitute the pitches of the gratings and the wavelength of the X-ray source.

PRIOR ART

Patent Document

Patent Document 1: Japanese Patent Laid-Open No. 2012-16370

SUMMARY OF THE INVENTION

Problem to be Solved by the Invention

Here, when an X-ray source that radiates X-rays having a continuous wavelength distribution (hereinafter referred to as the "continuous X-rays") is used as the X-ray source, it is not known which wavelength should be substituted in the mathematical formulas unlike the case in which an X-ray source that radiates X-rays having only a certain wavelength is used as the X-ray source. Therefore, in the X-ray imaging apparatus disclosed in Japanese Patent Laid-Open No. 2012-16370, there is a problem that it is difficult to determine the arrangement of the gratings when continuous X-rays are used.

The present invention has been proposed in order to solve the aforementioned problem, and an object of the present invention is to provide an X-ray phase contrast imaging apparatus capable of determining the arrangement of gratings even when continuous X-rays are used.

Means for Solving the Problem

In order to attain the aforementioned object, an X-ray phase contrast imaging apparatus according to a first aspect of the present invention includes an X-ray source that radiates continuous X-rays, a first grating irradiated with the continuous X-rays from the X-ray source to form a self-image, a second grating irradiated with the continuous X-rays that have passed through the first grating, and a detector that detects the continuous X-rays that have passed through the second grating. The X-ray source, the first grating, and the second grating are arranged so as to satisfy conditions of following formulas (1) and (2):

$$R1:d1=R:d2 \tag{1}$$

where d1 represents a pitch of the first grating, d2 represents a pitch of the second grating, R1 represents a distance between the X-ray source and the first grating, R2 represents a distance between the first grating and the second grating, and R represents R1+R2, and $$\frac{C}{r} > 1 \tag{2}$$

where C represents a difference between a maximum value and a minimum value of a signal curve that represents pixel value changes, and r represents a noise intensity of the signal curve that represents the pixel value changes.

In the X-ray phase contrast imaging apparatus according to the first aspect of the present invention, as described above, the X-ray source, the first grating, and the second grating are arranged so as to satisfy the condition of the formula (1). Thus, the X-ray source, the first grating, and the second grating can be arranged without using characteristics such as the wavelength of the X-ray source. Consequently, even when the continuous X-rays are used, the arrangement of the X-ray source, the first grating, and the second grating can be determined. Furthermore, the X-ray source, the first grating, and the second grating are arranged so as to satisfy the condition of the above formula (1), and thus the X-ray source, the first grating, and the second grating can be arranged so as to substantially match the pitch of the self-image of the first grating with the pitch of the second grating. Consequently, the X-ray source, the first grating, and the second grating can be arranged at positions suitable for imaging a subject. Furthermore, the X-ray source, the first grating, and the second grating are arranged so as to satisfy the condition of the above formula (2) such that the X-ray source, the first grating, and the second grating can be arranged so as to reduce noise. Consequently, a captured image with high visibility can be easily obtained.

An X-ray phase contrast imaging apparatus according to a second aspect of the present invention includes an X-ray source that radiates continuous X-rays, a first grating irradiated with the continuous X-rays from the X-ray source to form a self-image, a second grating irradiated with the continuous X-rays that have passed through the first grating, a detector that detects the continuous X-rays that have passed through the second grating, and a third grating arranged between the detector and the first grating. The first grating, the second grating, and the third grating are arranged so as to satisfy conditions of following formulas (3) and (4):

$$d0 = \frac{R1}{R2}d2 = \frac{R}{R2}d1 \tag{3}$$

where d0 represents a pitch of the third grating, d1 represents a pitch of the first grating, d2 represents a pitch of the second grating, R1 represents a distance between the third grating and the first grating, R2 represents a distance between the first grating and the second grating, and R represents R1+R2, and $$\frac{C}{r} > 1 \qquad (4)$$

where C represents a difference between a maximum value and a minimum value of a signal curve that represents pixel value changes, and r represents a noise intensity of the signal curve that represents the pixel value changes.

In the X-ray phase contrast imaging apparatus according to the second aspect of the present invention, as described above, the first grating, the second grating, and the third grating are arranged so as to satisfy the condition of the formula (3). Thus, similarly to the case of the aforementioned X-ray phase contrast imaging apparatus according to the first aspect, the arrangement of the first grating, the second grating, and the third grating can be determined even when the continuous X-rays are used. Furthermore, in this structure, the third grating is provided such that the continuous X-rays that have passed through the third grating can function as a plurality of X-ray sources. Consequently, a plurality of self-images of the first grating can be formed by the plurality of X-ray sources. In addition, the first grating, the second grating, and the third grating are arranged so as to satisfy the condition of the above formula (3) such that the first grating, the second grating, and the third grating can be arranged so as to substantially match the pitch of each of the self-images of the first grating with the pitch of the second grating. Consequently, the first grating, the second grating, and the third grating can be arranged at positions suitable for imaging a subject. Furthermore, the X-ray source, the first grating, and the second grating are arranged so as to satisfy the condition of the above formula (4) such that the first grating, the second grating, and the third grating can be arranged so as to reduce noise. Consequently, a captured image with high visibility can be easily obtained.

In the aforementioned X-ray phase contrast imaging apparatus according to the first aspect and the second aspect, the X-ray source, the first grating, and the second grating, or the first grating, the second grating, and the third grating are preferably arranged so as to further satisfy a condition of a following formula (5):

$$\frac{2v}{\sigma} > 1 \qquad (5)$$

where v represents visibility, and σ represents a noise intensity with respect to an average value of the signal curve that represents the pixel value changes.

According to this structure, in consideration of the visibility, the X-ray source, the first grating, and the second grating, or the first grating, the second grating, and the third grating can be arranged so as to reduce noise.

In the aforementioned structure in which the condition of the formula (5) is further satisfied, the visibility in the formula (5) is preferably defined by a following formula (6), or when a following formula (7) is defined, the visibility in the formula (5) is preferably defined by a following formula (8):

$$v = \frac{Imax - Imin}{Imax + Imin} \qquad (6)$$

where v represents the visibility, Imax represents a maximum value of the signal curve that represents the pixel value changes, and Imin represents a minimum value of the signal curve that represents the pixel value changes, and $$S(x, y) = \sum_{k=1}^{M} Ik(x, y) \exp\left(-\frac{2i\pi k}{M}\right) \text{ and} \qquad (7)$$

$$V(x, y) = \frac{2 \cdot |S(x, y)|}{\sum_{k=1}^{M} I_k(x, y)} \qquad (8)$$

where V(x, y) represents the visibility, k represents a predetermined point of the signal curve that represents the pixel value changes, Ik(x, y) represents a signal value at the predetermined point, x and y represent coordinate positions in a plane orthogonal to an irradiation axis direction of X-rays in the second grating, and M represents a total number of predetermined points.

Effect of the Invention

As described above, according to the present invention, the X-ray phase contrast imaging apparatus capable of determining the arrangement of the gratings even when the continuous X-rays are used can be provided.

MODES FOR CARRYING OUT THE INVENTION

Embodiments embodying the present invention are hereinafter described on the basis of the drawings.

First Embodiment (Structure of X-Ray Phase Contrast Imaging Apparatus)

The structure of an X-ray phase contrast imaging apparatus 100 according to a first embodiment of the present invention is described with reference to FIG. 1. In the following description, a direction Z is defined as the irradiation axis direction of X-rays radiated from an X-ray source 1, and directions X and Y are defined as directions orthogonal to each other in a plane orthogonal to the direction Z.

Figure 1:
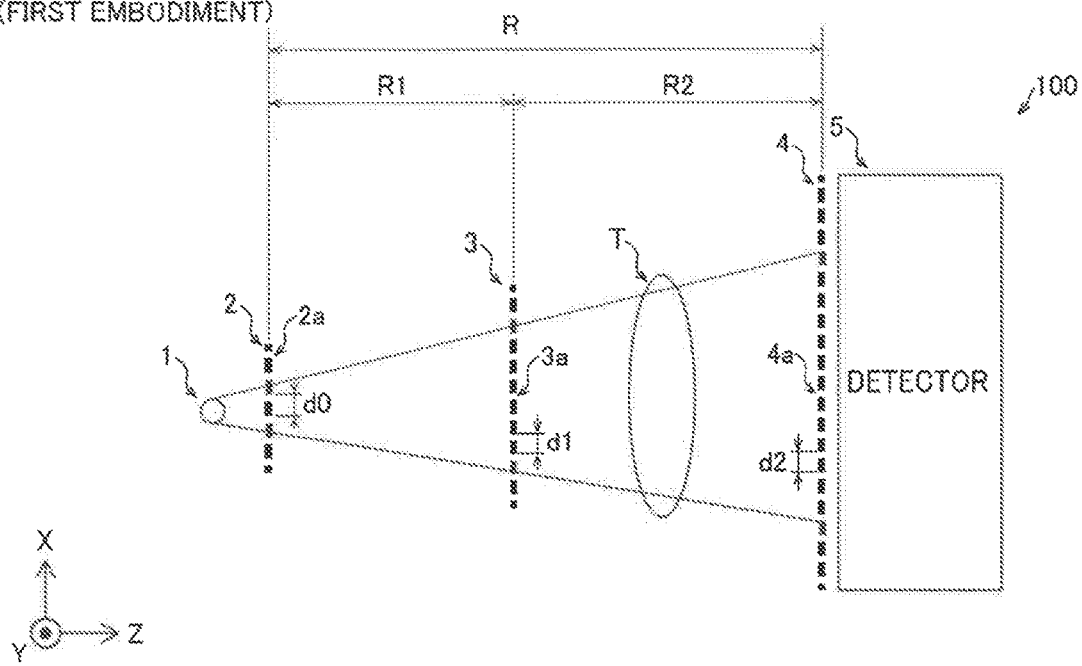
FIG. 1 is a diagram showing the overall structure of an X-ray phase contrast imaging apparatus according to a first embodiment of the present invention.

As shown in FIG. 1, the X-ray phase contrast imaging apparatus 100 is an apparatus that images the inside of a subject T using the phase contrast of X-rays that have passed through the subject T. For example, in medical applications, the X-ray phase contrast imaging apparatus 100 can be used to image the inside of the subject T as a living body. Furthermore, for example, in non-destructive inspection applications, the X-ray phase contrast imaging apparatus 100 can be used to image the inside of the subject T as an object.

As shown in FIG. 1, the X-ray phase contrast imaging apparatus 100 includes the X-ray source 1, a third grating 2, a first grating 3, a second grating 4, and a detector 5. The X-ray source 1, the third grating 2, the first grating 3, the second grating 4, and the detector 5 are arranged side by side in this order in the X-ray irradiation axis direction (direction Z).

The X-ray source 1 generates X-rays when a high voltage is applied thereto and radiates the generated X-rays. The X-ray source 1 radiates continuous X-rays having a continuous wavelength distribution.

The third grating 2 is a diffraction grating (absorption grating, so-called multi slit) that changes the intensity of the passing X-rays. The third grating 2 includes a plurality of slits 2a arrayed at a pitch d0 in the direction X orthogonal to the X-ray irradiation axis direction.

The third grating 2 is arranged between the X-ray source 1 and the first grating 3, and X-rays are radiated thereto from the X-ray source 1. The third grating 2 is provided to increase the coherence of the X-rays radiated from the X-ray source 1. The third grating 2 allows the X-rays that have passed through the respective slits 2a to function as line light sources (line light sources 21 and 22 described below, for example) corresponding to the positions of the respective slits 2a. Thus, the third grating 2 can increase the coherence of the X-rays that have passed through the third grating 2.

The first grating 3 is a diffraction grating (phase grating) that changes the phase of the passing X-rays. The first grating 3 includes a plurality of slits 3a arrayed at a pitch d1 in the direction X orthogonal to the X-ray irradiation axis direction.

The first grating 3 is arranged between the third grating 2 and the second grating 4, and the X-rays that have passed through the third grating 2 are radiated thereto. The first grating 3 is arranged at a position away from the third grating 2 by a distance R1. That is, the distance R1 is a distance between the third grating 2 and the first grating 3. The first grating 3 is provided to form a self-image. In the X-ray phase contrast imaging apparatus 100, the third grating 2 is provided to increase the coherence of the X-rays such that the self-image of the first grating 3 can be more reliably formed.

The second grating 4 is a diffraction grating (absorption grating) that changes the intensity of the passing X-rays. The second grating 4 includes a plurality of slits 4a arrayed at a pitch d2 in the direction X orthogonal to the X-ray irradiation axis direction.

The second grating 4 is arranged between the first grating 3 and the detector 5, and the X-rays that have passed through the first grating 3 are radiated thereto. The second grating 4 is arranged at a position away from the first grating 3 by a distance R2. That is, the distance R2 is a distance between the first grating 3 and the second grating 4. The second grating 4 interferes with the self-image of the first grating 3 to form Moire fringes.

Figure 6:
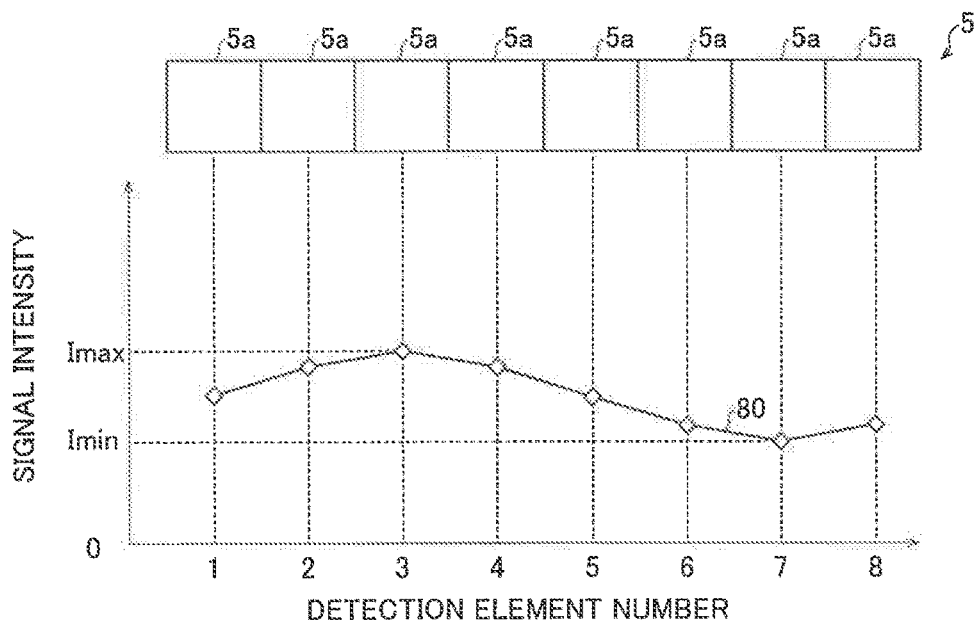
FIG. 6 is a diagram illustrating signal intensity changes under a method using a Fourier transform method.

The detector 5 detects the X-rays and converts the detected X-rays into an electric signal (detection signal). In the X-ray phase contrast imaging apparatus 100, the inside of the subject T is imaged based on the detection signal. The detector 5 is an FPD (Flat Panel Detector), for example. The detector 5 includes a plurality of detection elements 5a (see FIG. 6). In FIG. 6, only some of the detection elements 5a are shown. The plurality of detection elements 5a are arrayed side by side in vertical and horizontal directions at a predetermined pitch. Each of the detection elements 5a corresponds to a pixel of a captured image.

(Arrangement of Gratings)

Next, the arrangement of the first grating 3, the second grating 4, and the third grating 2 is described with reference to FIGS. 2 to 4.

According to the first embodiment, the first grating 3, the second grating 4, and the third grating 2 are arranged so as to satisfy the conditions of the following formula (9).

[Mathematical Formula 9]

$$d0 = \frac{R1}{R2}d2 = \frac{R}{R2}d1 \tag{9}$$

In the formula (9), the relationship between the first grating 3 and the second grating 4 and the relationship between the third grating 2 and the second grating 4 are defined.

<Relationship Between First Grating and Second Grating>

The right-hand equality in the formula (9) defines the relationship between the first grating 3 and the second grating 4. The right-hand equality in the formula (9) can be expressed by the following formula (10). [Mathematical Formula 10]

$$R1:d1=R:d2 \tag{10}$$

The formula (10) defines the arrangement of the first grating 3, the second grating 4, and the third grating 2 such that the pitch of the self-image of the first grating 3 substantially matches the pitch d2 of the second grating 4. The formula (10) can be obtained from the geometric arrangement of the first grating 3, the second grating 4, and the third grating 2. This point is described with reference to FIGS. 2 and 3.

Figure 2:
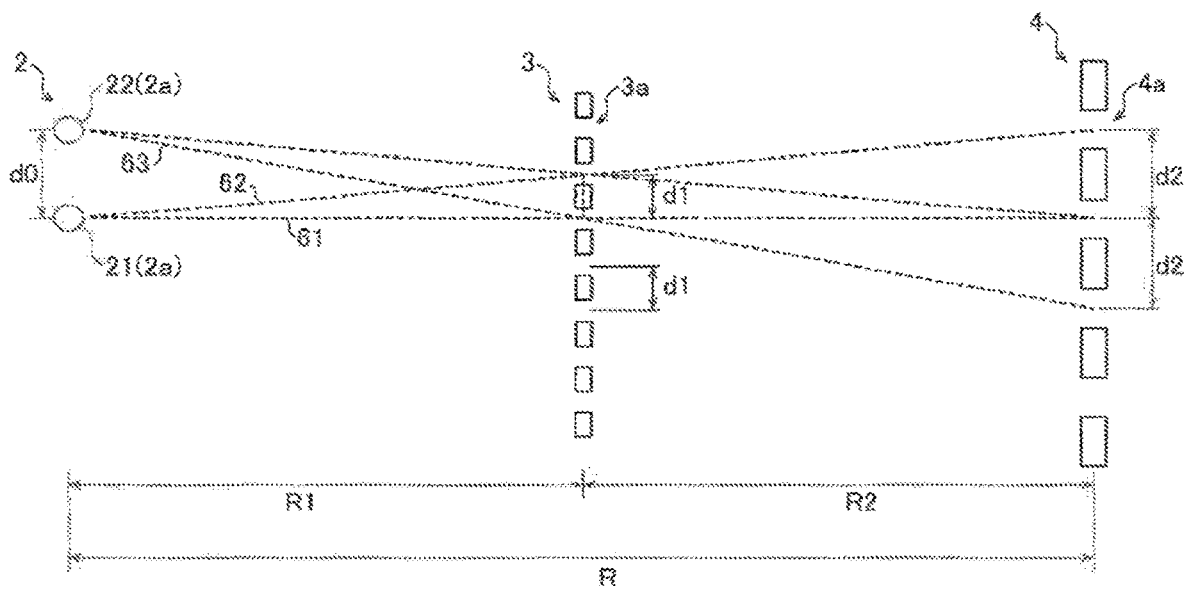
FIG. 2 is a diagram illustrating the arrangement of a first grating, a second grating, and a third grating of the X-ray phase contrast imaging apparatus according to the first embodiment.

The case in which X-rays are radiated from the line light source 21 corresponding to a slit 2a of the third grating 2 as shown in FIG. 2 is considered. In this case, the X-rays radiated from the line light source 21 spread, and thus on the downstream side in the irradiation axis direction relative to the first grating 3, the self-image of the first grating 3 more enlarged than the size of the first grating 3 is formed. In order to substantially match the pitch of the enlarged self-image of the first grating 3 with the pitch d2 of the second grating 4, it is only necessary to satisfy the geometric conditions shown in FIG. 3.

Figure 3:
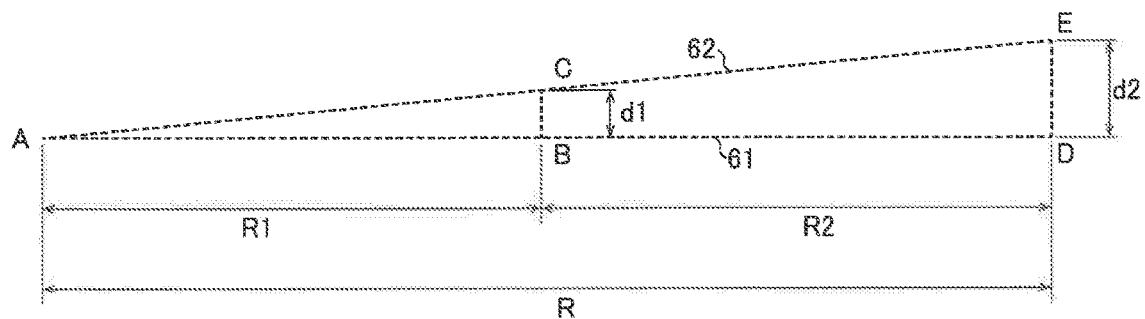
FIG. 3 is a diagram illustrating the relationship between the first grating and the second grating of the X-ray phase contrast imaging apparatus according to the first embodiment.

FIG. 3 shows a triangle ABC and a triangle ADE similar to the triangle ABC. A line segment AD of the triangle ADE corresponds to a line segment 61 that represents the trajectory of the X-rays radiated from the line light source 21 shown in FIG. 2. Furthermore, a line segment AE of the triangle ADE corresponds to a line segment 62 that represents the trajectory of the X-rays radiated from the line light source 21 shown in FIG. 2. The position of the vertex A of the triangle ABC corresponds to the position of the third grating 2 (line light source 21). The position of a line segment BC of the triangle ABC corresponds to the position of the first grating 3 shown in FIG. 2. Furthermore, the position of a line segment DE of the triangle ADE corresponds to the position of the second grating 4 shown in FIG. 2.

In this case, the length of a line segment AB of the triangle ABC is R1. The length of the line segment BC of the triangle ABC is d1. The length of the line segment AD of the triangle ADE is R. The length of the line segment DE of the triangle ADE is d2. Note that the length of a line segment BD is R2.

In this case, the above formula (10) in which a ratio between the distance R1 and the pitch d1 is equal to a ratio between the distance R and the pitch d2 can be derived from the similarity relationship of the triangle that a ratio between the line segment AB and the line segment BC is equal to a ratio between the line segment AD and the line segment DE.

The geometric conditions shown in FIG. 3 are satisfied such that the pitch of the self-image of the first grating 3 is increased from d1 to d2 at a position downstream from the position of the first grating 3 by the distance R2 in the irradiation axis direction. Consequently, the first grating 3, the second grating 4, and the third grating 2 are arranged so as to satisfy the conditions of the above formula (10) such that the first grating 3, the second grating 4, and the third grating 2 can be arranged so as to substantially match the pitch of the self-image of the first grating 3 with the pitch d2 of the second grating 4.

<Relationship Between Third Grating and Second Grating>

The left-hand equality in the formula (9) defines the relationship between the third grating 2 and the second grating 4. The left-hand equality in the formula (9) can be expressed by the following formula (11). [Mathematical Formula 11]

$$R1:R2=d0:d2 \quad (11)$$

In the X-ray phase contrast imaging apparatus 100, as described above, the X-rays that have passed through the third grating 2 are allowed to function as a plurality of X-ray sources (line light sources). Consequently, in the X-ray phase contrast imaging apparatus 100, the self-image of the first grating 3 is formed for each of the plurality of X-ray sources (line light sources).

The formula (11) defines the arrangement of the third grating 2 and the second grating 4 in which the pitch of the self-image of the first grating 3 for each of the plurality of X-ray sources (line light sources) substantially matches the pitch d2 of the second grating 4. The formula (11) can be obtained from the geometric arrangement of the first grating 3, the second grating 4, and the third grating 2. This point is described with reference to FIGS. 2 and 4.

The case in which X-rays are radiated from the line light source 21 corresponding to the slit 2a of the third grating 2 and the line light source 22 adjacent to the line light source 21 as shown in FIG. 2 is considered. In this case, the X-rays radiated from the line light source 21 spread, and thus on the downstream side in the irradiation axis direction relative to the first grating 3, the self-image of the first grating 3 more enlarged than the size of the first grating 3 is formed. Similarly, the self-image of the first grating 3 more enlarged than the size of the first grating 3 is also formed by the X-rays radiated from the line light source 22.

Figure 4:
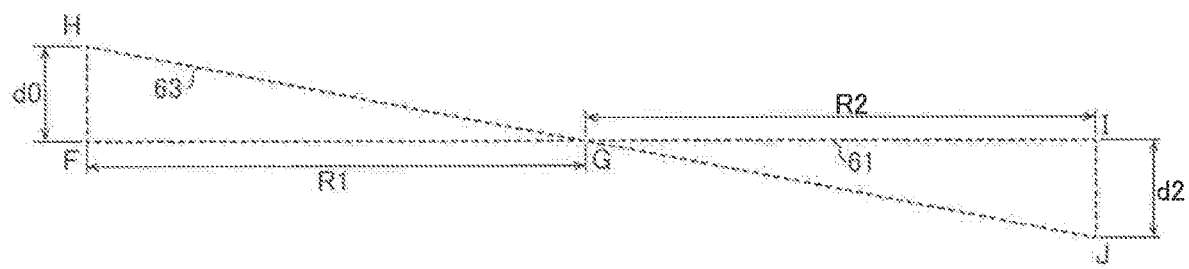
FIG. 4 is a diagram illustrating the relationship between the third grating and the second grating of the X-ray phase contrast imaging apparatus according to the first embodiment.

In this case, in order to substantially match the pitch of the self-image of the first grating 3 for each of the plurality of X-ray sources (such as the line light sources 21 and 22) with the pitch d2 of the second grating 4, it is only necessary to satisfy the geometric conditions shown in FIG. 4.

FIG. 4 shows a triangle FGH and a triangle IGJ similar to the triangle FGH. A line segment FI corresponds to the line segment 61 that represents the trajectory of the X-rays radiated from the line light source 21 shown in FIG. 2. A line segment HJ corresponds to a line segment 63 that represents the trajectory of the X-rays radiated from the line light source 22 shown in FIG. 2. The position of the vertex F of the triangle FGH corresponds to the position of the line light source 21 shown in FIG. 2. The position of the vertex H of the triangle FGH corresponds to the position of the line light source 22 shown in FIG. 2. The position of the vertex G of the triangle FGH corresponds to the position of the first grating 3 shown in FIG. 2. The position of a line segment IJ of the triangle IGJ corresponds to the position of the second grating 4 shown in FIG. 2.

In this case, the length of a line segment FG of the triangle FGH is R1. The length of a line segment FH of the triangle FGH is d0. The length of a line segment GI of the triangle IGJ is R2. The length of the line segment IJ of the triangle IGJ is d2. Note that the length of the line segment FI is R.

In this case, the above formula (11) in which a ratio between the distance R1 and the distance R2 is equal to a ratio between the pitch d0 and the pitch d2 can be derived from the similarity relationship of the triangle that a ratio between the line segment FG and the line segment GI is equal to a ratio between the line segment FH and the line segment IJ.

The geometric conditions shown in FIG. 4 are satisfied such that the pitch of the self-image of the first grating 3 formed by the line light source 21 and the pitch of the self-image of the first grating 3 formed by the line light source 22 are deviated by d2 (one pitch) at a position downstream from the position of the third grating 2 by the distance R in the irradiation axis direction. Consequently, the first grating 3, the second grating 4, and the third grating 2 are arranged so as to satisfy the conditions of the above formula (11) such that the first grating 3, the second grating 4, and the third grating 2 can be arranged so as to substantially match the pitch of the self-image of the first grating 3 for each of the plurality of X-ray sources (such as the line light sources 21 and 22) with the pitch d2 of the second grating 4.

(Determination of Grating Arrangement in Consideration of Noise)

Next, determination of the arrangement of the first grating 3, the second grating 4, and the third grating 2 in consideration of noise is described with reference to FIGS. 5 to 7. First, the signal curve acquired in the X-ray phase contrast imaging apparatus 100 is described with reference to FIGS. 5 and 6.

Figure 5:
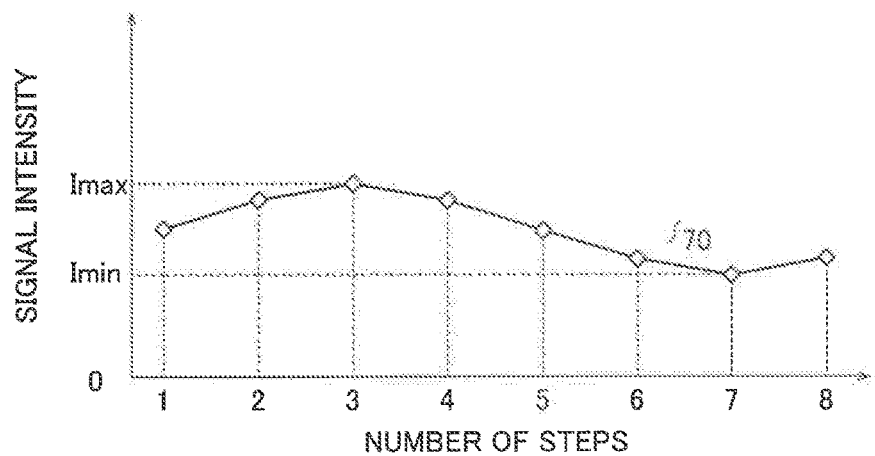
FIG. 5 is a diagram illustrating signal intensity changes under a fringe scanning method.

FIG. 5 shows a signal curve 70 obtained by a fringe scanning method. In the fringe scanning method, X-ray imaging is performed by stepping one of the first grating 3, the second grating 4, and the third grating 2 a plurality of times along a grating plane, and the inside of the subject T is imaged based on a plurality of Moire images obtained by X-ray imaging for each step.

In the fringe scanning method, a signal value (signal intensity) is obtained for each step. The signal curve 70 is a curve obtained by normalizing a pixel value (signal value) of each step in the signal detection element 5a of the detector 5. That is, the signal curve 70 is a signal curve that represents pixel value changes in the detector 5. Note that the pixel value is not limited to the pixel value of each step in the signal detection element 5a of the detector 5. For example, in the case of a pixel block including the plurality of detection elements 5a of the detector 5, a characteristic value (an average value or the center value of a histogram, for example) of each step in the pixel block including the plurality of detection elements 5a of the detector 5 may be used as the pixel value.

FIG. 6 shows a signal curve 80 obtained by a method using a Fourier transform method. In the method using the Fourier transform method, X-ray imaging is performed in a state in which one of the first grating 3, the second grating 4, and the third grating 2 is rotated in the grating plane, and the inside of the subject T is imaged based on a single Moire image obtained by this X-ray imaging.

In the method using the Fourier transform method, the signal curve 80 is a curve obtained by normalizing a pixel value of each of the detection elements 5a arrayed in a row, for example. That is, the signal curve 80 is a signal curve that represents pixel value changes in the detector 5. Note that the pixel value is not limited to the pixel value of each of the detection elements 5a arrayed in a row. For example, in the case of the pixel block including the plurality of detection elements 5a of the detector 5, a characteristic value (an average value or the center value of a histogram, for example) of each of pixel blocks arrayed in a row may be used as the pixel value.

As described above, in the X-ray phase contrast imaging apparatus 100, the signal curves 70 and 80 that represent pixel value changes are obtained by the fringe scanning method and the method using the Fourier transform method, for example.

According to the first embodiment, the first grating 3, the second grating 4, and the third grating 2 are arranged so as to further satisfy the conditions of the following formula (12).

[Mathematical Formula 12]

$$\frac{C}{r} > 1 \qquad (12)$$

Figure 7:
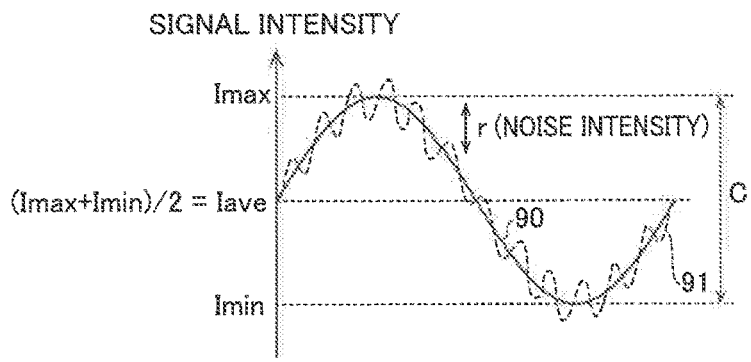
FIG. 7 is a diagram illustrating an example of noise in a signal curve.

As shown in FIG. 7, C is a difference between a maximum value (Imax) and a minimum value (Imin) of a signal curve 90 that represents pixel value changes. In addition, r is the noise intensity of the signal curve 90. Note that the signal curve 90 indicates a concept including the signal curves 70 and 80. The formula (12) defines a condition in which the intensity r of a noise 91 is smaller than the difference C between Imax and Imin. If the intensity r of the noise 91 is larger than the difference C between Imax and Imin, the signal curve 90 is buried in the noise 91. The noise 91 includes a quantum noise determined from the dose of X-rays and the electrical noise of the detector 5.

According to the first embodiment, the first grating 3, the second grating 4, and the third grating 2 are arranged so as to further satisfy the conditions of the following formula (13).

[Mathematical Formula 13]

$$\frac{2v}{\sigma} > 1 \qquad (13)$$

Here, v is visibility. In addition, σ is the noise intensity with respect to the average value (Iave=(Imax+Imin)/2) of the signal curve 90 as expressed by the following formula (14).

[Mathematical Formula 14]

$$\sigma = \frac{r}{\frac{Imax + Imin}{2}} \qquad (14)$$

According to the first embodiment, the visibility in the formula (13) is defined by the following formula (15), or when the following formula (16) is defined, the visibility in the formula (13) is defined by the following formula (17).

[Mathematical Formula 15]

$$v = \frac{Imax - Imin}{Imax + Imin} \qquad (15)$$

[Mathematical Formula 16]

$$S(x, y) = \sum_{k=1}^{M} I_k(x, y) \exp\left(-\frac{2i\pi k}{M}\right) \qquad (16)$$

[Mathematical Formula 17]

$$V(x, y) = \frac{2 \cdot |S(x, y)|}{\sum_{k=1}^{M} I_k(x, y)} \qquad (17)$$

Here, v in the formula (15) is visibility (i.e. v in the formula (13)). In addition, Imax in the formula (15) is the maximum value of the signal curve 90. Furthermore, Imin in the formula (15) is the minimum value of the signal curve 90.

The variables in the formulas (16) and (17) are different between the case of the fringe scanning method and the case of the method using the Fourier transform method, and thus the variables are described separately.

In the case of fringe scanning, V(x, y) in the formulas (16) and (17) is visibility (i.e. v in the formula (13)). Furthermore, x and y of V(x, y) are coordinate positions in the plane orthogonal to the X-ray irradiation axis direction (direction Z) in the second grating 4, x is a coordinate position in the direction X, and y is a coordinate position in the direction Y. In addition, k in the formulas (16) and (17) is the number of steps of the signal curve 70 shown in FIG. 5. Moreover, $I_k$(x, y) in the formulas (16) and (17) is a signal value (signal intensity) at the number of steps k. Furthermore, M in the formulas (16) and (17) is the total number of steps of the signal curve 70 (i.e. eight times in FIG. 5).

In the case of the method using the Fourier transform method, V(x, y) in the formulas (16) and (17) is visibility (i.e. v in the formula (13)). Furthermore, x and y of V(x, y) are coordinate positions in the plane orthogonal to the X-ray irradiation axis direction (direction Z) in the second grating 4, x is a coordinate position in the direction X, and y is a coordinate position in the direction Y. In addition, k in the formulas (16) and (17) is the detection element number of the signal curve 80 shown in FIG. 6. Furthermore, $I_k(x, y)$ in the formulas (16) and (17) is a signal value (signal intensity) at the detection element number k. In addition, M in the formulas (16) and (17) is the total number of detection elements of the signal curve 80 (i.e. eight in FIG. 6).

Here, the above formula (13) can be obtained from the formula (12).

First, the left-hand side of the formula (12) can be expressed by the following formula (18).

[Mathematical Formula 18]

$$\frac{C}{r} = \frac{Imax - Imin}{\frac{\sigma}{2}(Imax + Imin)} \quad (18)$$

Then, when the formula (15) is used as the visibility, the left-hand side of the formula (12) can be expressed by the following formula (19).

[Mathematical Formula 19]

$$\frac{C}{r} = \frac{Imax - Imin}{\frac{\sigma}{2}(Imax + Imin)} = \frac{2v}{\sigma} \quad (19)$$

Therefore, using the formula (19), the above formula (13) can be obtained from the formula (12).

(Results of Visibility Measurement)

Figure 8:
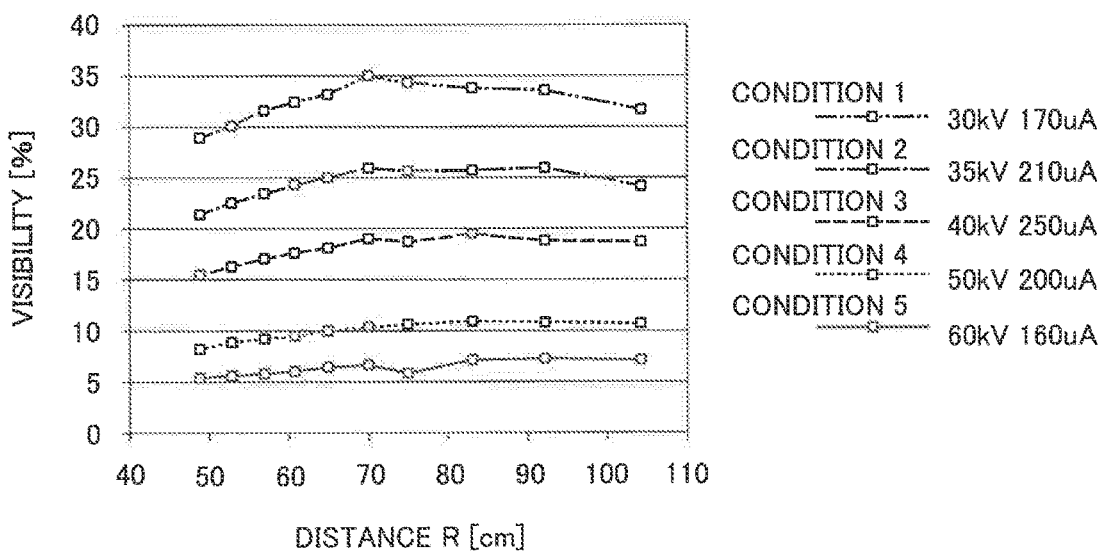
FIG. 8 is a graph showing the results of visibility measurement performed to confirm the effect of the first embodiment.

Next, the results of visibility measurement performed to confirm the effect of the first embodiment are shown with reference to FIG. 8. Here, the pitch d0 of the third grating 2 was set to 10 μm, the pitch d1 of the first grating 3 was set to 5 μm, the pitch d2 of the second grating 4 was set to 10 μm, and the first grating 3, the second grating 4, and the third grating 2 were arranged so as to satisfy the condition of the above formula (9). In addition, the visibility was measured by changing the distance R between the third grating 2 and the second grating 4, the tube voltage of the X-ray source 1, and the tube current of the X-ray source 1. The visibility was calculated using the above formula (17).

As shown in FIG. 8, in Condition 1, when the tube voltage of the X-ray source 1 was 30 kV and the tube current of the X-ray source 1 was 170 μA, the distance R was varied between about 50 cm and about 105 cm. In Condition 1, even when the distance R is varied between about 50 cm and about 105 cm, the value of the visibility is generally stable between about 29% and about 35%. Therefore, in Condition 1, it was possible to obtain the stable visibility in the irradiation axis direction.

In Condition 2, when the tube voltage of the X-ray source 1 was 35 kV and the tube current of the X-ray source 1 was 210 μA, the distance R was varied between about 50 cm and about 105 cm. In Condition 2, even when the distance R is varied between about 50 cm and about 105 cm, the value of the visibility is generally stable between about 22% and about 26%. Therefore, in Condition 2, it was possible to obtain the stable visibility in the irradiation axis direction.

In Condition 3, when the tube voltage of the X-ray source 1 was 40 kV and the tube current of the X-ray source 1 was 250 μA, the distance R was varied between about 50 cm and about 105 cm. In Condition 3, even when the distance R is varied between about 50 cm and about 105 cm, the value of the visibility is generally stable between about 16% and about 19%. Therefore, in Condition 3, it was possible to obtain the stable visibility in the irradiation axis direction.

In Condition 4, when the tube voltage of the X-ray source 1 was 50 kV and the tube current of the X-ray source 1 was 200 μA, the distance R was varied between about 50 cm and about 105 cm. In Condition 4, even when the distance R is varied between about 50 cm and about 105 cm, the value of the visibility is generally stable between about 8% and about 11%. Therefore, in Condition 4, it was possible to obtain the stable visibility in the irradiation axis direction.

In Condition 5, when the tube voltage of the X-ray source 1 was 60 kV and the tube current of the X-ray source 1 was 160 μA, the distance R was varied between about 50 cm and about 105 cm. In Condition 5, even when the distance R is varied between about 50 cm and about 105 cm, the value of the visibility is generally stable between about 6% and about 8%. Therefore, in Condition 5, it was possible to obtain the stable visibility in the irradiation axis direction.

Therefore, it has been confirmable that the first grating 3, the second grating 4, and the third grating 2 are arranged so as to satisfy the condition of the above formula (9) such that the stable visibility is obtained in the irradiation axis direction even when the tube voltage of the X-ray source 1 and the tube current of the X-ray source 1 are varied. That is, it has been confirmable that the condition of the above formula (9) is satisfied such that the first grating 3, the second grating 4, and the third grating 2 can be arranged at positions suitable for imaging the subject T even when the continuous X-rays are used.

Next, the case of determining the arrangement of the first grating 3, the second grating 4, and the third grating 2 in consideration of the noise of the signal curve is described with reference to FIG. 9. Here, the case of arranging the first grating 3, the second grating 4, and the third grating 2 so as to further satisfy the condition of the above formula (13) is described.

For example, assuming that σ in the formula (13) is 0.5, it is necessary to arrange the first grating 3, the second grating 4, and the third grating 2 so as to satisfy v>0.25. That is, it is necessary to arrange the first grating 3, the second grating 4, and the third grating 2 such that the value of the visibility becomes larger than 25%.

Figure 9:
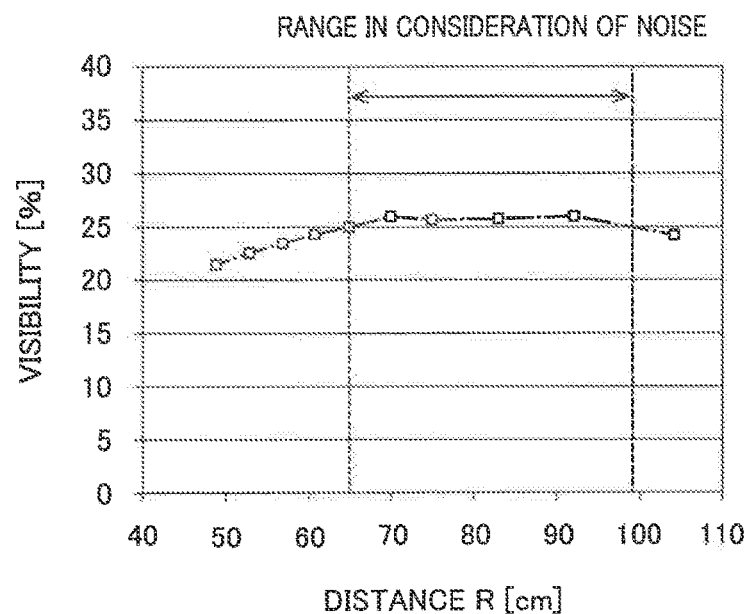
FIG. 9 is a diagram illustrating the possible range of a distance R in consideration of noise.

FIG. 9 shows the case of applying this condition in Condition 2 in FIG. 8. In this case, it is necessary to determine the distance R between about 65 cm and about 99 cm in order to satisfy the condition of the formula (13), as shown in FIG. 9. That is, the possible range of the distance R in consideration of noise is about 65 cm to about 99 cm.

Effects of First Embodiment

According to the first embodiment, the following effects are achieved.

According to the first embodiment, as described above, the first grating 3, the second grating 4, and the third grating 2 are arranged so as to satisfy the condition of the formula (9). Thus, the first grating 3, the second grating 4, and the third grating 2 can be arranged without using characteristics such as the wavelength of the X-ray source 1. Consequently, even when the continuous X-rays are used, the arrangement of the first grating 3, the second grating 4, and the third grating 2 can be determined. According to the first embodiment, as described above, the third grating 2 is provided such that the continuous X-rays that have passed through the third grating 2 are allowed to function as the plurality of X-ray sources (line light sources 21 and 22, for example). Consequently, a plurality of self-images of the first grating 3 can be formed by the plurality of X-ray sources. Furthermore, the first grating 3, the second grating 4, and the third grating 2 are arranged so as to satisfy the condition of the above formula (9) such that the first grating 3, the second grating 4, and the third grating 2 can be arranged so as to substantially match the pitch of each of the self-images of the first grating 3 with the pitch d2 of the second grating 4. Consequently, the first grating 3, the second grating 4, and the third grating 2 can be arranged at positions suitable for imaging the subject T. Furthermore, the first grating 3, the second grating 4, and the third grating 2 are arranged so as to satisfy the condition of the above formula (12). Thus, the first grating 3, the second grating 4, and the third grating 2 can be arranged so as to reduce noise. Consequently, a captured image with high visibility can be easily obtained.

According to the first embodiment, as described above, the first grating 3, the second grating 4, and the third grating 2 are arranged so as to further satisfy the condition of the formula (13). Thus, in consideration of visibility, the first grating 3, the second grating 4, and the third grating 2 can be arranged so as to reduce noise.

According to the first embodiment, as described above, the visibility in the formula (13) is defined by the formula (15), or when the formula (16) is defined, the visibility in the formula (13) is defined by the formula (17).

Second Embodiment

Next, a second embodiment is described with reference to FIG. 10. In this second embodiment, an example in which a third grating is not provided unlike the aforementioned first embodiment in which the third grating is provided is described. The same structures as those of the aforementioned first embodiment are denoted by the same reference numerals in the drawings, and description thereof is omitted.
(Structure of X-ray Phase Contrast Imaging Apparatus)

Figure 10:
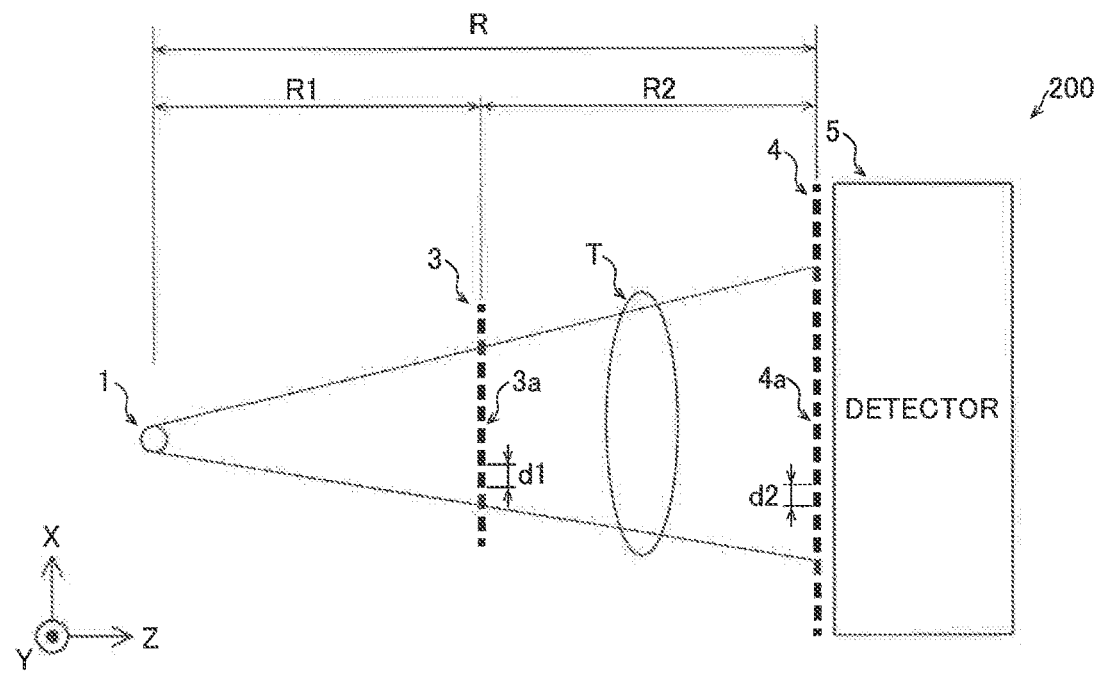
FIG. 10 is a diagram showing the overall structure of an X-ray phase contrast imaging apparatus according to a second embodiment of the present invention.

As shown in FIG. 10, an X-ray phase contrast imaging apparatus 200 according to the second embodiment of the present invention is different from the X-ray phase contrast imaging apparatus 100 according to the aforementioned first embodiment in that the third grating 2 according to the aforementioned first embodiment is not provided.

According to the second embodiment, an X-ray source 1, a first grating 3, and a second grating 4 are arranged so as to satisfy the condition of the following formula (20).
[Mathematical Formula 20]

$$R1{:}d1 = R{:}d2 \qquad (20)$$

Here, d1 is the pitch of the first grating 3, d2 is the pitch of the second grating 4, and R1 is a distance between the X-ray source 1 and the first grating 3. In addition, R2 is a distance between the first grating 3 and the second grating 4, and R is R1+R2.

The formula (20) is the same formula as the formula (10) according to the aforementioned first embodiment. That is, the formula (20) defines the arrangement of the first grating 3 and the second grating 4 so as to substantially match the pitch of the self-image of the first grating 3 with the pitch d2 of the second grating 4. The formula (20) can be obtained from the geometric arrangement of the X-ray source 1, the first grating 3, and the second grating 4. This point is analogous to that in the first embodiment when the line light source 21 according to the aforementioned first embodiment is replaced with the X-ray source 1, and thus description thereof is omitted. According to the second embodiment, the X-ray source 1, the first grating 3, and the second grating 4 are arranged so as to satisfy the above formulas (12) and (13) similarly to the aforementioned first embodiment.

The remaining structures of the second embodiment are similar to those of the aforementioned first embodiment.

Effects of Second Embodiment

According to the second embodiment, the following effects are achieved.

According to the second embodiment, as described above, the X-ray source 1, the first grating 3, and the second grating 4 are arranged so as to satisfy the condition of the formula (20). Thus, the X-ray source 1, the first grating 3, and the second grating 4 can be arranged without using characteristics such as the wavelength of the X-ray source 1. Consequently, even when continuous X-rays are used, the arrangement of the X-ray source 1, the first grating 3, and the second grating 4 can be determined. Furthermore, the X-ray source 1, the first grating 3, and the second grating 4 are arranged so as to satisfy the condition of the above formula (20) such that the X-ray source 1, the first grating 3, and the second grating 4 can be arranged so as to substantially match the pitch of the self-image of the first grating 3 with the pitch d2 of the second grating 4. Consequently, the X-ray source 1, the first grating 3, and the second grating 4 can be arranged at positions suitable for imaging a subject T. Furthermore, the X-ray source 1, the first grating 3, and the second grating 4 are arranged so as to satisfy the condition of the above formula (12) such that the X-ray source 1, the first grating 3, and the second grating 4 can be arranged so as to reduce noise. Consequently, a captured image with high visibility can be easily obtained.

The remaining effects of the second embodiment are similar to those of the aforementioned first embodiment.

Modified Examples

The embodiments disclosed this time must be considered as illustrative in all points and not restrictive. The scope of the present invention is not shown by the above description of the embodiments but by the scope of claims for patent, and all modifications (modified example) within the meaning and scope equivalent to the scope of claims for patent are further included.

For example, while the example in which the subject is placed on the side of the first grating closer to the detector has been shown in each of the aforementioned first and second embodiments, the present invention is not restricted to this. According to the present invention, the subject may not be placed on the side of the first grating closer to the detector. For example, the subject may be placed on the side of the first grating opposite to the detector.

While the example in which the first grating, the second grating, and the third grating are arranged so as to satisfy the conditions of the formulas (12) and (13) has been shown in the aforementioned first embodiment, and the example in which the X-ray source, the first grating, and the second grating are arranged so as to satisfy the conditions of the formulas (12) and (13) has been shown in the aforementioned second embodiment, the present invention is not restricted to this. According to the present invention, as long as the condition of the formula (9) is satisfied, the first grating, the second grating, and the third grating may not be arranged so as to satisfy the conditions of the formulas (12) and (13). As long as the condition of the formula (20) is satisfied, the X-ray source, the first grating, and the second grating may not be arranged so as to satisfy the conditions of the formulas (12) and (13).

While the example in which the first grating is a diffraction grating (phase grating) that changes the phase of the passing X-rays has been shown in each of the aforementioned first and second embodiments, the present invention is not restricted to this. According to the present invention, the first grating may be a diffraction grating (absorption grating) that changes the intensity of the passing X-rays.

DESCRIPTION OF REFERENCE NUMERALS

1 X-ray source
2 third grating
3 first grating
4 second grating
5 detector
100, 200 X-ray phase contrast imaging apparatus

The invention claimed is:

1. An X-ray phase contrast imaging apparatus comprising:
an X-ray source that radiates continuous X-rays;
a first grating irradiated with the continuous X-rays from the X-ray source to form a self-image;
a second grating irradiated with the continuous X-rays that have passed through the first grating; and
a detector that detects the continuous X-rays that have passed through the second grating, wherein
the X-ray source, the first grating, and the second grating are arranged so as to satisfy conditions of following formulas (1) and (2):

$$R1:d1 = R:d2 \quad (1)$$

where d1 represents a pitch of the first grating, d2 represents a pitch of the second grating, R1 represents a distance between the X-ray source and the first grating, R2 represents a distance between the first grating and the second grating, and R represents R1+R2, and $$\frac{C}{r} > 1 \quad (2)$$

where C represents a difference between a maximum value and a minimum value of a signal curve that represents pixel value changes, and r represents a noise intensity of the signal curve that represents the pixel value changes.

2. The X-ray phase contrast imaging apparatus according to claim 1, wherein
the X-ray source, the first grating, and the second grating are arranged so as to further satisfy a condition of a following formula (5):

$$\frac{2v}{\sigma} > 1 \quad (5)$$

where v represents visibility, and σ represents a noise intensity with respect to an average value of the signal curve that represents the pixel value changes.

3. The X-ray phase contrast imaging apparatus according to claim 2, wherein the visibility in the formula (5) is defined by a following formula (6), or when a following formula (7) is defined, the visibility in the formula (5) is defined by a following formula (8):

$$v = \frac{I\max - I\min}{I\max + I\min} \quad (6)$$

where v represents the visibility, Imax represents a maximum value of the signal curve that represents the pixel value changes, and Imin represents a minimum value of the signal curve that represents the pixel value changes, and $$S(x, y) = \sum_{k=1}^{M} Ik(x, y)\exp\left(-\frac{2i\pi k}{M}\right) \quad (7)$$

and $$V(x, y) = \frac{2 \cdot |S(x, y)|}{\sum_{k=1}^{M} I_k(x, y)} \quad (8)$$

where V(x, y) represents the visibility, k represents a predetermined point of the signal curve that represents the pixel value changes, Ik(x, y) represents a signal value at the predetermined point, x and y represent coordinate positions in a plane orthogonal to an irradiation axis direction of X-rays in the second grating, and M represents a total number of predetermined points.

4. An X-ray phase contrast imaging apparatus comprising:
an X-ray source that radiates continuous X-rays;
a first grating irradiated with the continuous X-rays from the X-ray source to form a self-image;
a second grating irradiated with the continuous X-rays that have passed through the first grating;
a detector that detects the continuous X-rays that have passed through the second grating; and
a third grating arranged between the X-ray source and the first grating, wherein
the first grating, the second grating, and the third grating are arranged so as to satisfy conditions of following formulas (3) and (4):

$$d0 = \frac{R1}{R2}d2 = \frac{R}{R2}d1 \quad (3)$$

where d0 represents a pitch of the third grating, d1 represents a pitch of the first grating, d2 represents a pitch of the second grating, R1 represents a distance between the third grating and the first grating, R2 represents a distance between the first grating and the second grating, and R represents R1+R2, and $$\frac{C}{r} > 1 \quad (4)$$

where C represents a difference between a maximum value and a minimum value of a signal curve that represents pixel value changes, and r represents a noise intensity of the signal curve that represents the pixel value changes.

5. The X-ray phase contrast imaging apparatus according to claim 4, wherein
the first grating, the second grating, and the third grating are arranged so as to further satisfy a condition of a following formula (5):

$$\frac{2v}{\sigma} > 1 \tag{5}$$

where v represents visibility, and σ represents a noise intensity with respect to an average value of the signal curve that represents the pixel value changes.

6. The X-ray phase contrast imaging apparatus according to claim 5, wherein
the visibility in the formula (5) is defined by a following formula (6), or when a following formula (7) is defined, the visibility in the formula (5) is defined by a following formula (8):

$$v = \frac{Imax - Imin}{Imax + Imin} \tag{6}$$

where v represents the visibility, Imax represents a maximum value of the signal curve that represents the pixel value changes, and Imin represents a minimum value of the signal curve that represents the pixel value changes, and $$S(x, y) = \sum_{k=1}^{M} Ik(x, y)\exp\left(-\frac{2i\pi k}{M}\right) \text{ and} \tag{7}$$

$$V(x, y) = \frac{2 \cdot |S(x, y)|}{\sum_{k=1}^{M} I_k(x, y)} \tag{8}$$

where V(x, y) represents the visibility, k represents a predetermined point of the signal curve that represents the pixel value changes, Ik(x, y) represents a signal value at the predetermined point, x and y represent coordinate positions in a plane orthogonal to an irradiation axis direction of X-rays in the second grating, and M represents a total number of predetermined points.

* * * * *